(12) United States Patent
Karimi

(10) Patent No.: US 9,038,718 B1
(45) Date of Patent: May 26, 2015

(54) METHOD FOR LOST CIRCULATION REDUCTION IN DRILLING OPERATIONS

(71) Applicant: Schlumberger Technology Corporation, Sugar Land, TX (US)

(72) Inventor: Mojtaba Karimi, Houma, LA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 305 days.

(21) Appl. No.: 13/646,306

(22) Filed: Oct. 5, 2012

Related U.S. Application Data

(60) Provisional application No. 61/543,726, filed on Oct. 5, 2011.

(51) Int. Cl.
*E21B 21/00* (2006.01)
*E21B 33/138* (2006.01)
*C09K 8/03* (2006.01)

(52) U.S. Cl.
CPC ........... *E21B 21/003* (2013.01); *C09K 8/03* (2013.01); *E21B 33/138* (2013.01)

(58) Field of Classification Search
CPC ............................. E21B 21/003; E21B 33/138
USPC .............. 166/250.08, 250.1, 278, 292, 279, 166/305.1, 310; 175/46, 50
See application file for complete search history.

(56) References Cited

U.S. PATENT DOCUMENTS

| | | | |
|---|---|---|---|
| 8,006,761 B2 * | 8/2011 | Duncum et al. | 166/292 |
| 8,393,411 B2 * | 3/2013 | Dupriest et al. | 175/40 |
| 8,401,795 B2 * | 3/2013 | Kaageson-Loe et al. | 702/9 |
| 8,505,628 B2 * | 8/2013 | Panga et al. | 166/278 |
| 8,662,172 B2 * | 3/2014 | Panga et al. | 166/278 |
| 8,672,057 B2 * | 3/2014 | DuPriest et al. | 175/65 |
| 8,726,990 B2 * | 5/2014 | Karcher et al. | 166/279 |
| 8,812,236 B1 * | 8/2014 | Freeman et al. | 702/6 |
| 8,813,873 B2 * | 8/2014 | Beardmore et al. | 175/72 |
| 2005/0167159 A1 * | 8/2005 | Bailey et al. | 175/72 |
| 2009/0188718 A1 * | 7/2009 | Kaageson-Loe et al. | 175/40 |
| 2010/0181065 A1 * | 7/2010 | Ladva et al. | 166/250.01 |
| 2010/0181073 A1 * | 7/2010 | Dupriest et al. | 166/308.1 |
| 2010/0300760 A1 * | 12/2010 | Beardmore et al. | 175/72 |
| 2011/0056683 A1 * | 3/2011 | Duncum et al. | 166/276 |
| 2011/0094950 A1 * | 4/2011 | Dahl | 210/85 |
| 2011/0247812 A1 * | 10/2011 | Panga et al. | 166/278 |
| 2012/0000641 A1 * | 1/2012 | Panga et al. | 166/51 |
| 2012/0000651 A1 * | 1/2012 | Panga et al. | 166/278 |
| 2013/0087331 A1 * | 4/2013 | Karcher et al. | 166/279 |
| 2013/0146294 A1 * | 6/2013 | DuPriest et al. | 166/308.1 |
| 2014/0041870 A1 * | 2/2014 | Sanders et al. | 166/292 |
| 2014/0146314 A1 * | 5/2014 | Ronaes et al. | 356/336 |

OTHER PUBLICATIONS

Moji Karimi et al.; "Formation Damage and Fluid Loss Reduction due to Plastering Effect of Casing Drilling"; Jun. 2011 (11 pages).

* cited by examiner

*Primary Examiner* — Jennifer H Gay
(74) *Attorney, Agent, or Firm* — Osha Liang LLP

(57) ABSTRACT

A method may include determining a first particle size distribution for particulate additives in a first wellbore fluid circulated through a wellbore through an earthen formation, and determining a second particle size distribution for drilled cuttings resulting from drilling of the wellbore. The first and second particle size distributions may then be compared to determine a third particle size distribution for the combined particulate additives and the drilled cuttings. A lost circulation material having a fourth particle size distribution may then be selected based on the third particle size distribution and the selected lost circulation material may be pumped into the wellbore.

13 Claims, 5 Drawing Sheets

METHOD FOR LOST CIRCULATION REDUCTION IN DRILLING OPERATIONS

BACKGROUND

During the drilling of a wellbore, various fluids are typically used in the well for a variety of functions. The fluids may be circulated through a drill pipe and drill bit into the wellbore, and then may subsequently flow upward through the wellbore to the surface. During this circulation, the drilling fluid may act to remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

As stated above, wellbore fluids are circulated downhole to remove rock, as well as deliver agents to combat the variety of issues described above. Fluid compositions may be water- or oil-based and may comprise weighting agents, surfactants, proppants, and polymers. However, for a wellbore fluid to perform all of its functions and allow wellbore operations to continue, the fluid must stay in the borehole. Frequently, undesirable formation conditions are encountered in which substantial amounts or, in some cases, practically all of the wellbore fluid may be lost to the formation. For example, wellbore fluid can leave the borehole through large or small fissures or fractures in the formation or through a highly porous rock matrix surrounding the borehole.

Lost circulation is a recurring drilling problem, characterized by loss of drilling mud into downhole formations. It can occur naturally in formations that are fractured, highly permeable, porous, cavernous, or vugular. These earth formations can include shale, sands, gravel, shell beds, reef deposits, limestone, dolomite, and chalk, among others.

Lost circulation may also result from induced pressure during drilling. Specifically, induced mud losses may occur when the mud weight, required for well control and to maintain a stable wellbore, exceeds the fracture resistance of the formations. A particularly challenging situation arises in depleted reservoirs, in which the drop in pore pressure weakens hydrocarbon-bearing rocks, but neighboring or inter-bedded low permeability rocks, such as shales, maintain their pore pressure. This can make the drilling of certain depleted zones impossible because the mud weight required to support the shale exceeds the fracture resistance of the sands and silts.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method that includes determining a first particle size distribution for particulate additives in a first wellbore fluid circulated through a wellbore through an earthen formation; determining a second particle size distribution for drilled cuttings resulting from drilling of the wellbore; comparing the first and second particle size distributions to determine a third particle size distribution for the combined particulate additives and the drilled cuttings; selecting a lost circulation material having a fourth particle size distribution based on the third particle size distribution; and pumping the selected lost circulation material into the wellbore.

In another aspect, embodiments disclosed herein relate to a method that includes determining a first particle size distribution for drilled cuttings resulting from drilling of a wellbore or an offset well; selecting a lost circulation material having a second particle size distribution based on the first particle size distribution; and pumping a wellbore fluid with particulate additives and the selected lost circulation material into the wellbore.

In yet another aspect, embodiments disclosed herein relate to a method, that includes collecting a wellbore fluid circulated through a drill string and into an annulus between a borehole wall and the drill string, wherein the drill string is configured to provide a continuous or semi-continuous contact with the wall, wherein the wellbore fluid contains particulate additives, and wherein the collected wellbore fluid contains the particulate additives and drilled cuttings having a first particle size distribution; and selecting a lost circulation material having a size range where there is a lower volume percentage of particles than surrounding size ranges in the first particle size distributions.

Other aspects and advantages of the claimed subject matter will be apparent from the following description and the appended claims.

DETAILED DESCRIPTION

In one aspect, embodiments disclosed herein relate to method of reducing fluid losses during drilling operations. Particular aspects may relate to the use of lost circulation materials during casing drilling and the selection of the lost circulation materials based on the wellbore fluid particulates and the drilled cuttings.

As used herein "casing drilling" refers to a drilling operation in which a well is drilled and cased simultaneously. Specifically, the casing string (which is to be cemented or otherwise permanently installed in the wellbore) is used as the drill string with the drill bit being attached at the distal end thereof. Wellbore fluids may be pumped through the interior of the drill (casing) string and into the annulus between the drill (casing) string and formation walls. As the bit grinds and gouges the earth formation into cuttings (referred to as drilled cuttings), the wellbore fluid is ejected out of openings in the bit to life the drilled cuttings off the bottom of the hole and away from the bit, up towards the surface in the annular space between the drill (casing) string and the wall of the borehole.

Figure 1:
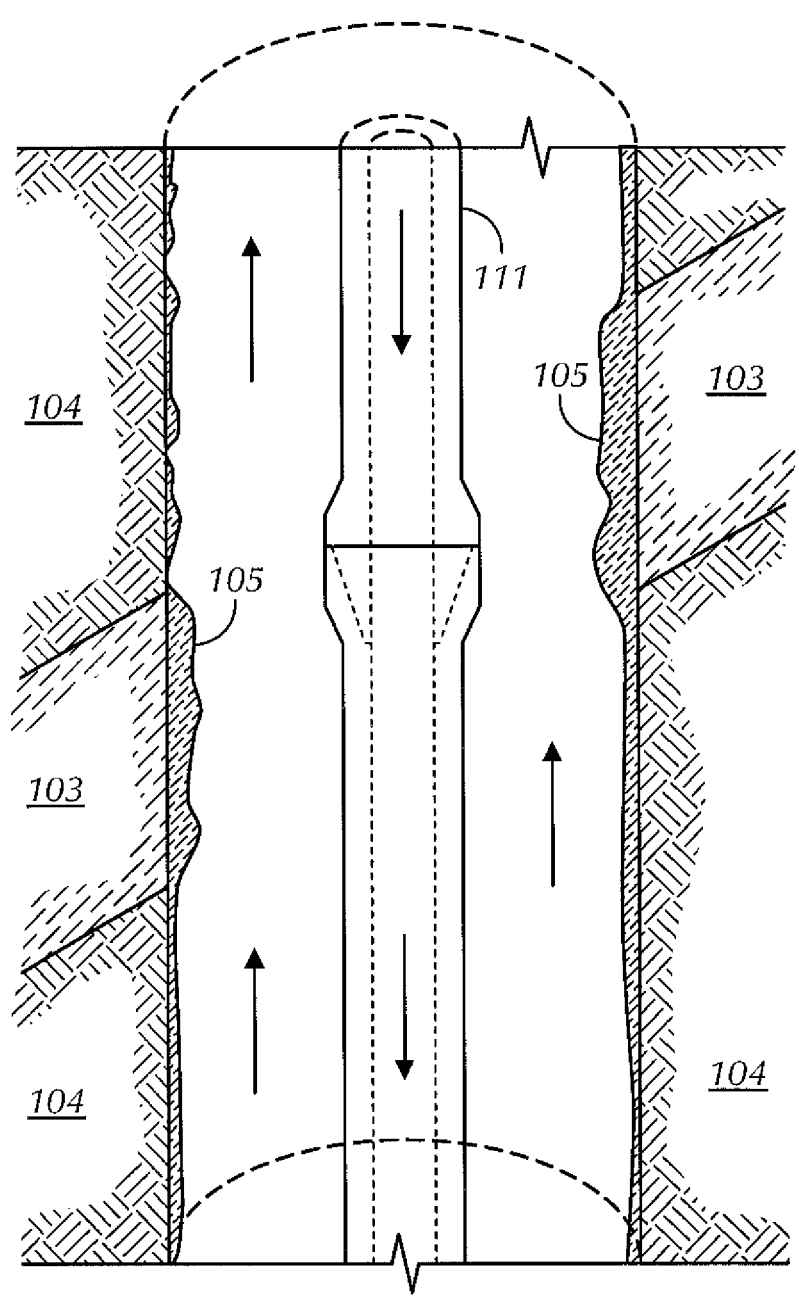
FIG. 1 is a schematic of an open hole well drilled with a bit attached to a drill string.
Figure 2:
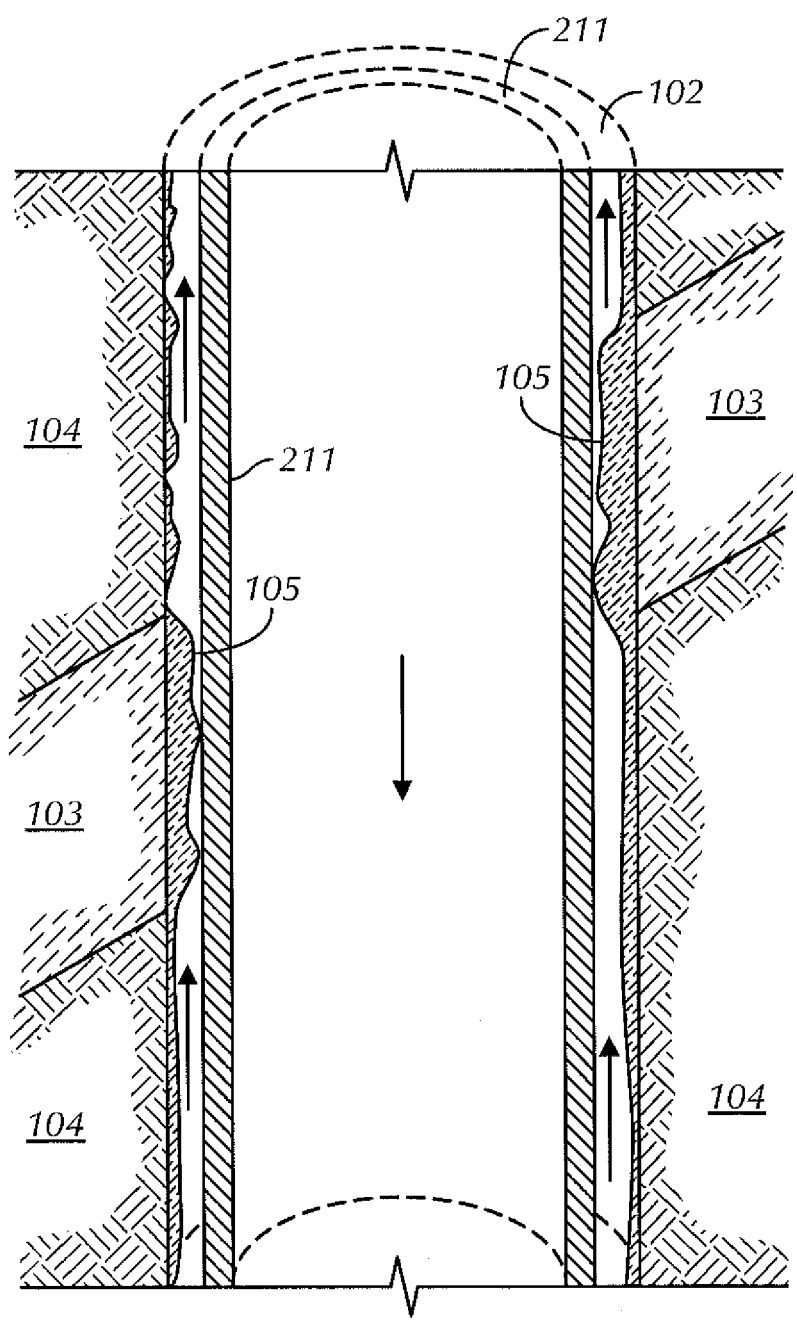
FIG. 2 is a schematic of an open hole well drilled with a bit attached to a casing string.

Referring now to FIG. 1 and FIG. 2, a section of a borehole drilled with conventional drill string is shown in FIG. 1 and a section of a borehole drilled by casing drilling is shown in FIG. 2. Like reference numbers are used to indicate like parts between FIGS. 1 and 2. As shown in FIG. 1, a section of the drill string 111 is in the center of an open, i.e., uncased, borehole 102. The borehole traverses a porous formation layer 103 embedded within layers of impermeable rock 104. A wellbore fluid is circulated through the drill string 111 and returns loaded with drilled cuttings through the annulus between the wall of the borehole 102 and the drill string 111, as indicated by arrows. During drilling operations, an amount of the fluidic components of the wellbore fluid may be absorbed by the formation, leaving behind a layer of solid particles 105, also referred to in the art as a filtercake.

Similar to the drilling operation using a conventional drill string 111 shown in FIG. 1, as shown in FIG. 2, a string 211 of pipe is in the center of the open borehole 102 that includes a porous formation layer 103 and layers of impermeable rock 104. However, instead of drill string 111, the well shown in FIG. 2 is drilled with a casing string 211 having a larger diameter than drill string 111. That is, a drill bit (not shown) is attached at the distal end of casing string 211. Further, whereas a drill string 111 would be retrieved from the well upon tripping the bit and upon completion of drilling, casing string 211 is left in the well to form the outer casing of the wellbore. The larger diameter of the casing string 211 as compared to the drill string 111 narrows the annular space between the casing string 211 and the wall of the well 102. As a result, during the drilling operation, casing string 211 asserts a continuous or semi-continuous force on and/or contact with the wall 102 and any filtercake 105 produced thereon.

In addition to contacting the wall 102 and filtercake 105, the reduced annular space may also result in the drilled cutting produced by the drill bit as it advances through the earthen formation to be ground into smaller particle sizes (and/or produce a larger particle size distribution) as compared to a conventionally drilled well (illustrated in FIG. 1). The finer drilled cuttings may be sufficiently small that the particles may adhere to the wellbore and help seal pore spaces and/or fractures to reduce filtration/fluid loss into the formation. However, in some instances, the drilled cuttings may be insufficient alone to prevent lost circulation.

As described above, lost circulation may be naturally occurring, the result of drilling through various formations such as unconsolidated formations having high permeability, naturally fractured formations including limestone, chalk, quartzite, and brittle shale, vugular or cavernous zones, etc.

Alternatively, lost circulation may be the result of drilling-induced fractures. For example, when the pore pressure (the pressure in the formation pore space provided by the formation fluids) exceeds the pressure in the open wellbore, the formation fluids tend to flow from the formation into the open wellbore. Therefore, the pressure in the open wellbore is typically maintained at a higher pressure than the pore pressure. While it is highly advantageous to maintain the wellbore pressures above the pore pressure, on the other hand, if the pressure exerted by the wellbore fluids exceeds the fracture resistance of the formation, a formation fracture and thus induced mud losses may occur. Further, with a formation fracture, when the wellbore fluid in the annulus flows into the fracture, the loss of wellbore fluid may cause the hydrostatic pressure in the wellbore to decrease, which may in turn also allow formation fluids to enter the wellbore. As a result, the formation fracture pressure typically defines an upper limit for allowable wellbore pressure in an open wellbore while the pore pressure defines a lower limit. Therefore, a major constraint on well design and selection of drilling fluids is the balance between varying pore pressures and formation fracture pressures or fracture gradients though the depth of the well.

A particularly challenging situation arises in depleted reservoirs, in which high pressured formations are neighbored by or inter-bedded with normally or abnormally pressured zones. For example, high permeability pressure depleted sands may be neighbored by high pressured low permeability rocks, such as shale or high pressure sands. This can make the drilling of certain depleted zones nearly impossible because the mud weight required to support the shale exceeds the fracture resistance of the pressure depleted sands and silts.

However, one skilled in the art would appreciate that, in addition to excessive mud weights, such induced fractures may also be partially caused by various drilling techniques or errors. For example, the incorrect placement of casing (too shallow of a placement) may result in an improper mud weight window based on the actual pore-pressure gradient, excessive downhole pressures contributed by any of rapid movement of pipe, excessive pump rates and velocities, improper hole cleaning, etc.

Addition of lost circulation materials (also referred to as LCMs) may aid in reducing, preventing, and/or stopping the loss of fluid to the formation. In accordance with embodiments of the present disclosure, the lost circulation may be reduced or prevented through the use of particulate based treatments (used alone or in combination with a cement or resin based treatment). Specifically, the present inventor has determined that lost circulation materials having a particle size distribution (PSD) in a particle size range in which the particles in the wellbore fluid either as particulate additives (such as weighting agent) or as drilled cuttings represent a lower volume fraction than the surrounding ranges. Specifically, there are three elements to the PSD of the fluid exposed to a fluid loss zone: the clean mud PSD (i.e., the particulate additive's particle size distribution), the generated drilled cuttings PSD, and the added lost circulation material PSD. When drilling a well, the clean mud PSD and the drilled cuttings PSD are already set by the selected fluid as well as nature of the formation and drilling parameters (bit type, casing side force, formation lithology, depth, etc.), but the lost circulation material may be varied on the fly and selected based on the PSD of the clean mud and the drilled cuttings.

Specifically, the methods of the present disclosure evaluates and determines the location within a broad size range where there is loss solid concentration, and a lost circulation material may be selected to have a particular size range (and concentration) to raise the solid concentration within that size range.

Figure 3:
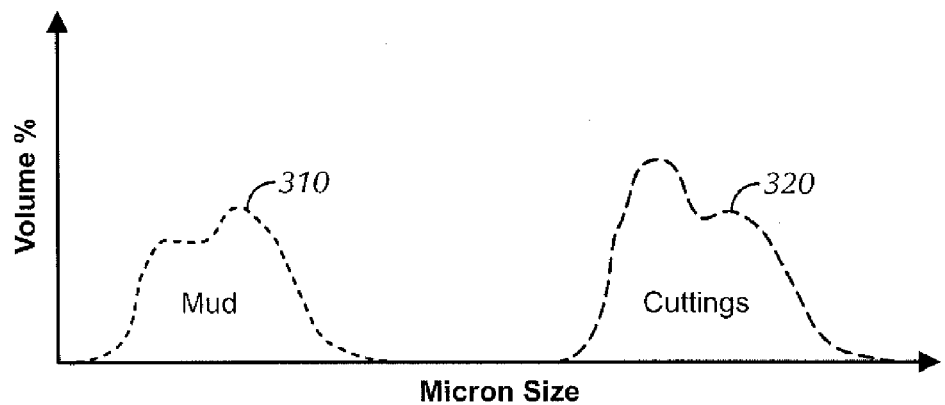
FIG. 3 shows a particle size distribution of a wellbore fluid and drilled cuttings.
Figure 4:
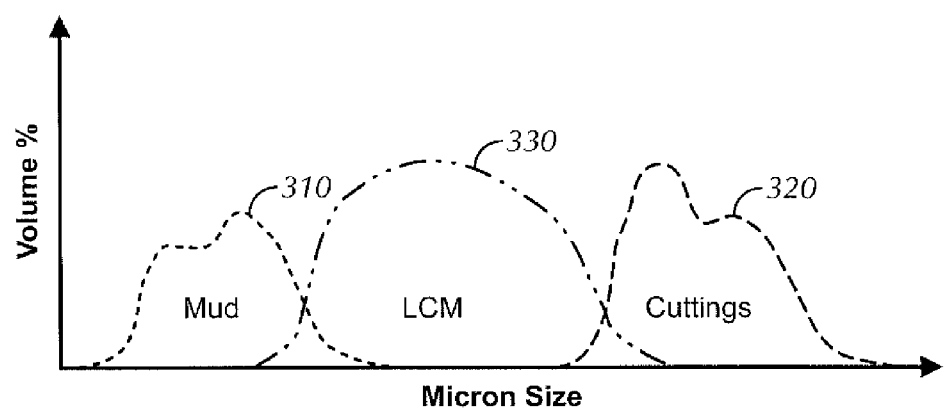
FIG. 4 shows the overlay of a particle size distribution of a wellbore fluid, drilled cuttings, and a lost circulation material.
Figure 5:
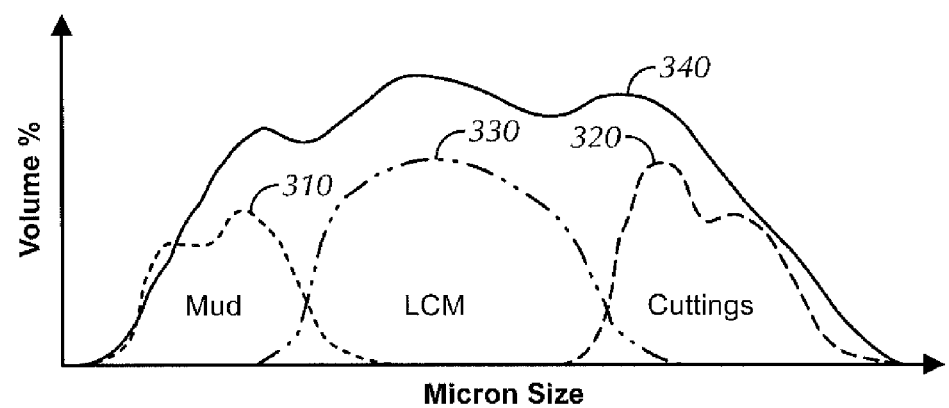
FIG. 5 shows the overlay of a particle size distribution of a wellbore fluid, drilled cuttings, and a lost circulation material and the total particle size distribution.

Referring now to FIG. 3, a schematic graph of a particle size distribution of particulates in a wellbore fluid (mud) 310 and drilled cuttings 320 is shown. As shown in FIG. 3, there exists a gap between the fluid particulates 310 and the drilled cuttings 320, in which there is a reduced (or no) volume of particles in the size range between the two types of particles that may be present in a wellbore fluid as it is carried to the surface through the annular space in the wellbore. Referring now to FIG. 4, a lost circulation material 330 may be added to the wellbore fluid, the lost circulation material 330 having a particle size distribution between that of the fluid particulates 310 and the drilled cuttings 320. Referring now to FIG. 5, the resulting particle size distribution of all solids 340 in a wellbore fluid as it returns to the surface (including fluid particulates 310, drilled cuttings 320, and lost circulation materials 330) may have no gaps (represented by a reduced volume fraction in a sub-range of the total particle size range) therein.

Thus, any gaps or reduced volume fractions in a sub-range may be filled by lost circulation materials.

Figure 6:
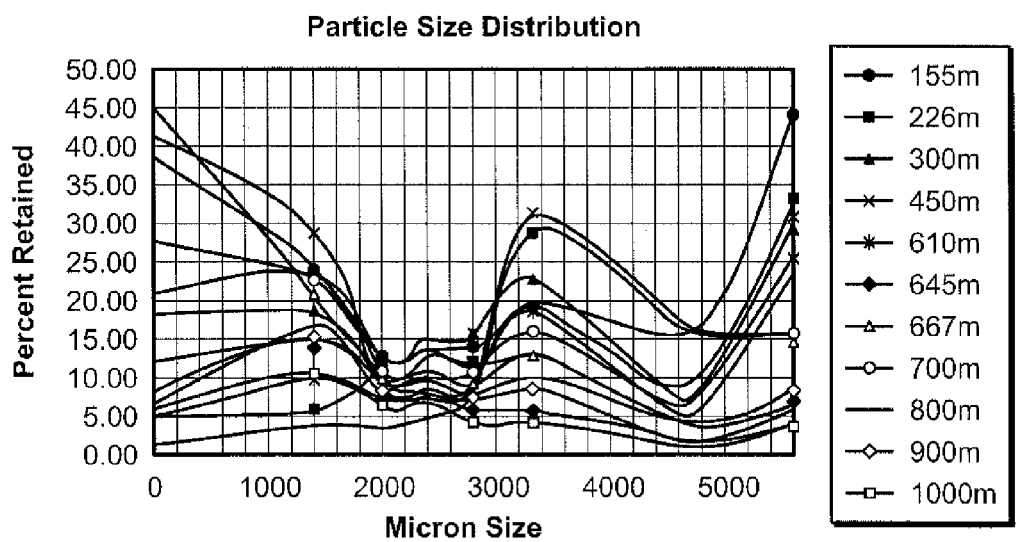
FIGS. 6-8 show particle size distributions of drilled cuttings resulting from casing drilling operations.
Figure 7:
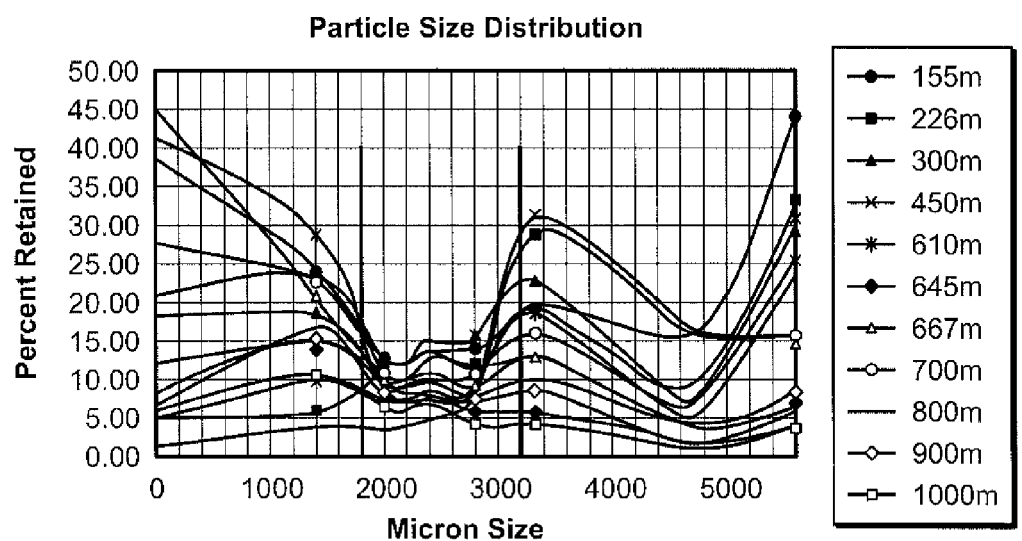
Figure 8:
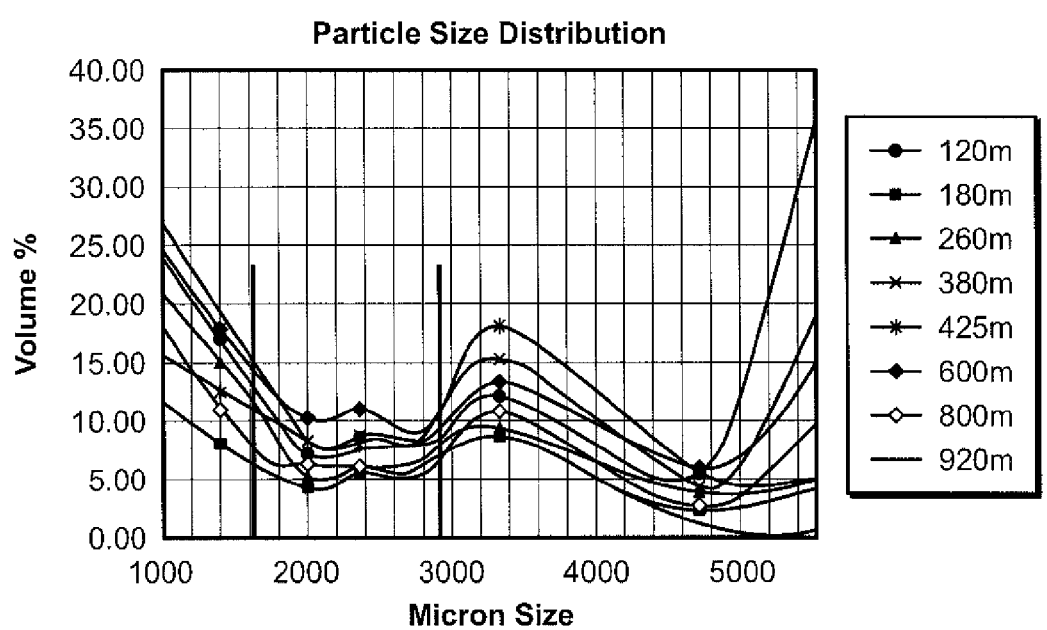

To achieve this result, the particle size distributions of fluid particulates (particulate additives) and drilled cuttings may both be determined, separately or in combination, depending on the stage at which the determination is made. For example, for a fluid have has been used in a drilling operation and collected at the surface, the collected fluid may be considered as a whole to determine a single particle size distribution for all solids in the circulated wellbore fluid (including particulate additives and drilled cuttings) or the drilled cuttings may be separated from the fluid and particulate additives based on separatory screening known in the art. Such determinations may include one or more of laser diffraction, sieve analysis, image analysis, etc. It is also within the scope of the present disclosure that the determination of the fluid's particulate additives may be based on knowledge of the PSD of the particulates without addition evaluation or analysis. It may also be that the PSD of the fluid particulates are sufficiently smaller than the drilled cuttings and substantially smaller than the size of particles needed reduce, prevent, or stop fluid loss into the formation, and in such instances, the gap in the particle size distribution may be a gap that exists solely within the range of the drilled cuttings. For example, referring now to FIGS. 6-8, plots of the PSD of three different casing drilling operations (showing the effect on the PSD at drilling to different depths) are presented, each showing a gap or reduced volume fraction for a sub-range of the entire PSD range. In such embodiments, only the distribution of the drilled cuttings needs to be determined and considered in selecting a PSD for a lost circulation material.

Thus, embodiments of the present disclosure may involve determining a first particle size distribution for particulate additives in a first wellbore fluid circulated through a wellbore through an earthen formation; determining a second particle size distribution for drilled cuttings resulting from drilling of the wellbore; comparing the first and second particle size distributions to determine a third particle size distribution for the combined particulate additives and the drilled cuttings; selecting a lost circulation material having a fourth particle size distribution based on the third particle size distribution; and pumping the selected lost circulation material into the wellbore.

In this and in all embodiments, the determining may include, for example, sequential laser diffraction of the wellbore fluid and dry sieve analysis of the drilled cuttings, and/or simultaneously analysis of the fluid particulates and drilled solid a returned wellbore fluid circulated through the wellbore through one or more laser diffraction and sieve analysis.

In this and in all embodiments, the comparing may include overlaying plots of the first and second particle size distribution and determining a size range where there is a lower volume percentage of particles than surrounding size ranges in the first and second particle size distributions.

Further, in this and in all embodiments, the particle size distribution of the lost circulation material may also be based, in part, on predicted fracture widths in the formation. Thus, the selection of the lost circulation material may generally included both size ranges and volume fraction (both forming a particle size distribution), and in the case of consideration of predicted fracture widths, both size range and volume fraction of the lost circulation material may be taken into consideration. Thus, when fracture width is also taken into consideration, the lost circulation material may also include two or more distinct modes of particle addition based on the fracture widths, and in such instance the PSD of the lost circulation material may be considered to have a multimodal particle size distribution. It is also within the scope of the present disclosure that such a multimodal distribution may be used even without consideration of predicted fracture width depending on the PSD of the particulates and/or drilled cuttings and any gaps that may exists in such total ranges.

Fracture width may either be calculated using drilling parameters and rock properties or estimated from the rate of fluid losses and the hydraulic pressure in the loss zone. For example, fracture gradient, Young's modulus, Poisson's ratio, well pressure, and hole size may be at least used to estimate the width of fractures, which may be done in pre-well planning or following loss occurrences. Such determinations may be made based on conventional fracture models known in the art, including modified Perkins-Kern-Nordgren (PKN) & Geertsma-de Klerk-Khristianovic (GdK) based fracture models. Once losses have occurred, however, one skilled in the art would appreciate that urgency may prevent precise calculation of the fracture apertures from the rock and well properties, and instead an estimation may be performed.

Further, as described herein, the selected lost circulation material may be pumped as a spot or squeeze treatment, such as after sudden losses of fluid volume have occurred, or may be added to a fluid being circulated through the drill string (as a background fluid additive) as a preventative or remedial measure. Further, as described above, such methods may find particular use when the drill string is a casing string that is in continuous or semi-continuous contact with the walls of the formation.

As mentioned above, in one or more embodiments, the selection of the lost circulation material may be based entirely on the PSD of drilled cuttings, which may include drilled cuttings from same wellbore needing treatment or instead from an offset well.

In the case of planning a well, it is also envisioned that the particulate additives may also be taken into consideration, whether or not the fluid (and particulate additives) have been used yet to drill a well, and in fact, it is also within the scope of the present application that the size range of the particulates may be modified in part based on the analysis of the drilled cuttings and selection of lost circulation material.

In addition to the particle size range of the lost circulation materials, selection may also consider the volume fractions, which may be based, in part, based on the type of fluid loss and the mechanism of treatment. Specifically, lost circulation treatments generally fall into two main categories: low fluid loss treatments where the fracture or formation is rapidly plugged and sealed; and high fluid loss treatments where dehydration of the loss prevention material in the fracture or formation with high leak off of a carrier fluid fills a fracture and/or forms a plug that then acts as the foundation for fracture sealing. The mechanism by which fluid loss is controlled, i.e., plugging, bridging, and filling, may be based on the particle size distribution, relative fracture aperture, fluid leak-off through the fracture walls, and fluid loss to the fracture tip.

In a low fluid loss treatment, a preliminary treatment may include a particulate-based treatment whereby the particles may enter the throat of a fracture, plug or bridge and seal the fracture. Conversely, high fluid loss treatments may operate by filling the fracture with particles. For particulate based treatments, the difference between such treatments is largely based on the particle sizes and particle sizes distribution in comparison to the fracture aperture.

For low fluid loss, particle-based treatments, a treatment blend solution based on a particle size distribution that follows the Ideal Packing Theory is designed to minimize fluid loss. Further discussion of selection of particle sizes required to initiate a bridge may be found in SPE 58793, which is herein incorporated by reference in its entirety. In order to achieve plugging or bridging, a particulate treatment may be selected based on particle type(s), particle geometry(s), concentration(s), and particle size distribution(s) so that coarse or very coarse particles plug or bridge the mouth of the fracture (or the oversized pores of the high permeability formation), and finer particles may then form a tight filtercake behind the bridging particles, thus affecting a seal and fluid loss control. However, in addition to such particulate based treatments, depending on the classified severity of loss, a reinforcing plug, including cement- or resin-based plugs, may be used in conjunction with the particulate treatment to seal off the fracture.

Conversely, for high fluid loss treatments, particulate based treatments typically use a relatively narrow (uniform) particle size distribution, with medium or fine particles, in order to promote fluid loss. Use of such particles may allow for the material to enter into and be deposited in the fracture by a process of dehydration as the carrier fluid in the LCM treatment leaks-off into the formation. High fluid loss treatments are typically only be used in high permeability formations or fractured formations where there already is a pre-existing high fluid loss, in the reservoir section, shallow poorly consolidated sands or carbonate lithologies.

Particulate-based treatments may include use of particles frequently referred to in the art as bridging materials. For example, such bridging materials may include at least one substantially crush resistant particulate solid such that the bridging material props open and bridges or plugs the fractures (cracks and fissures) that are induced in the wall of the wellbore. As used herein, "crush resistant" refers to a bridging material is physically strong enough to withstand the closure stresses exerted on the fracture bridge. Examples of bridging materials suitable for use in the present disclosure include graphite, calcium carbonate (preferably, marble), dolomite ($MgCO_3.CaCO_3$), celluloses, micas, proppant materials such as sands or ceramic particles and combinations thereof. Further, it is also envisaged that a portion of the bridging material may comprise drill cuttings having the desired average particle diameter in the range of 25 to 2000 microns.

The sizing of the bridging material may also be selected based on the size of the fractures predicted for a given formation. In one embodiment, the bridging material has an average particle diameter in the range of 50 to 1500 microns, and from 250 to 1000 microns in another embodiment. The bridging material may comprise substantially spherical particles; however, it is also envisaged that the bridging material may comprise elongate particles, for example, rods or fibers. Where the bridging material comprises elongate particles, the average length of the elongate particles should be such that the elongate particles are capable of bridging the induced fractures at or near the mouth thereof. Typically, elongate particles may have an average length in the range 25 to 2000 microns, preferably 50 to 1500 microns, more preferably 250 to 1000 microns. The bridging material may be sized so as to readily form a bridge at or near the mouth of the induced fractures. Typically, the fractures that may be plugged or filled with a particulate-based treatment may have a fracture width at the mouth in the range 0.1 to 5 mm. However, the fracture width may be dependent, amongst other factors, upon the strength (stiffness) of the formation rock and the extent to which the pressure in the wellbore is increased to above initial fracture pressure of the formation during the fracture induction (in other words, the fracture width is dependent on the pressure difference between the drilling mud and the initial fracture pressure of the formation during the fracture induction step).

In addition to bridging/propping open the fractures at their mouths, the bridge may also be sealed to prevent the loss of the bridge/material behind the bridge back into the wellbore. Depending on the material and/or particle size distribution selected as the bridging particles, and the material's sealing efficiency, it may be desirable to also include an optional bridge sealing material with the bridging material. However, one of ordinary skill in the art would appreciate that in some instances, a bridging material may possess both bridging and sealing characteristics, and thus, one additive may be both the bridging material and the bridge sealing material. Additionally, the use of a broad particle size distribution (and in particular, inclusion of fine bridging particles) may also be sufficient to seal the bridge formed at the mouth of the fracture. However, it may be desirable in other embodiments to also include a sealing material to further increase the strength of the seal. Additives that may be useful in increasing the sealing efficiency of the bridge may include such materials that are frequently used in loss circulation or fluid loss control applications. For example, such bridge sealing materials may include fine and/or deformable particles, such as industrial carbon, graphite, cellulose fibers, asphalt, etc. Moreover, one of ordinary skill in the art would appreciate that this list is not exhaustive, and that other sealing materials as known in the art may alternatively be used.

Embodiments of the present disclosure may allow for the remedial treatments of fluid loss during drilling as well as preventative treatments for fluid loss to be used in drilling operations incurring fluid loss, as well as during wellbore planning. Particularly, remedial treatment may allow for evaluation of the particle size distribution for the wellbore fluid and drilled cuttings to determine any gaps therein so that a lost circulation material may be added to fill the gaps to stop or reduce fluid loss once it has occurred.

In contrast, preventative treatments may allow for solutions to fluid loss to be built into wellbore plans to decrease fluid loss during subsequent drilling, through consideration of particle size distribution of the fluid and drilled cuttings from the same wellbore as well as from offset well data. Additionally, preventative treatments may be used as on-the-fly modifications to drilling plans when unexpected formation types are encountered during a drilling operation. Thus, preventative treatment solutions may be used in both wellbore planning and re-planning existing wellbore plans during drilling so that a lost circulation material may be provided as a background or continuous particle addition to the wellbore fluid to prevent or at least reduce the severity of potential future fluid loss.

Lost circulation treatments may be applied as, for example, a spot application or a squeeze treatment, or may be added to the wellbore fluid being used to drill the well along with the other particulate additives such as weighting agents, etc.

In one embodiment for a continuous particle addition while drilling a short interval, the loss control media may be added directed to the active pit or spotted at the drill bit. While drilling, the shaker screens may be either entirely bypassed, or alternatively, all except the scalping deck of a multiple deck vibratory separatory may be removed. Thus, the lost circulation materials may be directly recycled and retained in the wellbore fluid, thereby retaining a maximum amount of the lost circulation materials. However, such a configuration may result in large volumes of cuttings in the active system, and while the cuttings may assist the loss control media, the cuttings may also result in higher fluid rheology, wear on pumps, wear on logging while drilling tools, and risk plugging logging while drilling tools.

In another embodiment for a continuous particle addition while drilling an extended interval, it may be beneficial to use vibratory separators with a solids control system for adding and removing lost circulation materials in circulation. By managing the particles in circulation, the rheology of the fluid may be controlled and cuttings may be removed from the system resulting in less wear to system components. However, depending on the loss circulation material used, large volumes of material may be lost to separation, and as such, greater inventory of lost circulation materials will be required.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed:

1. A method, comprising:
   determining a first particle size distribution for particulate additives in a first wellbore fluid circulated through a wellbore through an earthen formation;
   determining a second particle size distribution for drilled cuttings resulting from drilling of the wellbore;
   comparing the first and second particle size distributions to determine a third particle size distribution for the combined particulate additives and the drilled cuttings, wherein the comparing comprises overlaying plots of the first and second particle size distribution and determining a size range where there is a lower volume percentage of particles than surrounding size ranges in the first and second particle size distributions;
   selecting a lost circulation material having a fourth particle size distribution based on the third particle size distribution; and
   pumping the selected lost circulation material into the wellbore.

2. The method of claim 1, wherein determining the first particle size distribution comprises laser diffraction of the wellbore fluid.

3. The method of claim 1, wherein determining the second particle size distribution comprises dry sieve analysis.

4. The method of claim 1, wherein determining the first particle size distribution and the second particle size distribution occurs at simultaneously through analysis of a returned wellbore fluid circulated through the wellbore.

5. The method of claim 1, wherein the determining the first particle size distribution and the second particle size distribution is performed sequentially.

6. The method of claim 1, wherein the fourth particle size distribution is further based on predicted fracture widths.

7. The method of claim 6, wherein the selecting further comprises selecting volume fractions for the lost circulation material based on the predicted fracture width.

8. The method of claim 1, wherein the selecting further comprises selecting a concentration of the lost circulation material.

9. The method of claim 1, wherein the fourth particle size distribution comprises a multimodal particle size distribution.

10. The method of claim 1, wherein the selected lost circulation material is pumped as a spot treatment.

11. The method of claim 1, wherein the selected lost circulation material is pumped with the wellbore fluid comprising the particulate additives.

12. The method of claim 11, wherein the pumping comprises circulating the wellbore fluid comprising the particulate additives and the selected lost circulation material through a drill string and into an annulus between the wall and the drill string such that a filter cake is deposited on the wall by the wellbore fluid, wherein the drill string is configured to provide a continuous or semi-continuous contact with the wall of the wellbore, and wherein the filter cake is compacted by contact with the drill string.

13. The method of claim 1, wherein the selecting occurs after losses of the wellbore fluid to the earthen formation occur.

* * * * *